(12) United States Patent
Chao

(10) Patent No.: US 6,806,064 B2
(45) Date of Patent: Oct. 19, 2004

(54) BACULOVIRUS ENHANCER-LIKE SEQUENCE

(75) Inventor: Yu-Chan Chao, Taipei (TW)

(73) Assignee: Academia Sinica, Taipei (TW)

( * ) Notice: Subject to any disclaimer, the term of this patent is extended or adjusted under 35 U.S.C. 154(b) by 256 days.

(21) Appl. No.: 10/191,177

(22) Filed: Jul. 9, 2002

(65) Prior Publication Data

US 2003/0082144 A1 May 1, 2003

Related U.S. Application Data

(60) Provisional application No. 60/305,513, filed on Jul. 13, 2001.

(51) Int. Cl.[7] ............ C12N 15/866; C12N 15/63; C12N 15/64; C12N 5/10; C07H 21/04
(52) U.S. Cl. .......... 435/69.1; 435/320.1; 435/325; 435/348; 536/23.1; 536/24.1; 536/23.72
(58) Field of Search ................. 435/320.1, 69.1, 435/325, 348; 536/23.1, 24.1, 23.72

(56) References Cited

PUBLICATIONS

Todd et al., J. Virol., 1995, vol. 69, No. 2, pp. 968–974.*
Lu et al., J. Virol., 1995, vol. 69, No. 2, pp. 975–982.*
Passarelli et al., J. Virol., 1993, vol. 67, No. 4, pp. 2149–2158.*
Possee et al., Virology, 1991, vol. 185, pp. 229–241.*

* cited by examiner

Primary Examiner—David Guzo
(74) Attorney, Agent, or Firm—Fish & Richardson P.C.

(57) ABSTRACT

The invention features nucleic acid constructs and related methods useful for the high level expression of a heterologous protein in a cell, e.g., an insect cell. The constructs include an enhancer-like sequence located upstream from the polyhedrin gene locus in the genome of baculovirus, which sequence enhances the activity of an operably linked promoter.

33 Claims, 11 Drawing Sheets

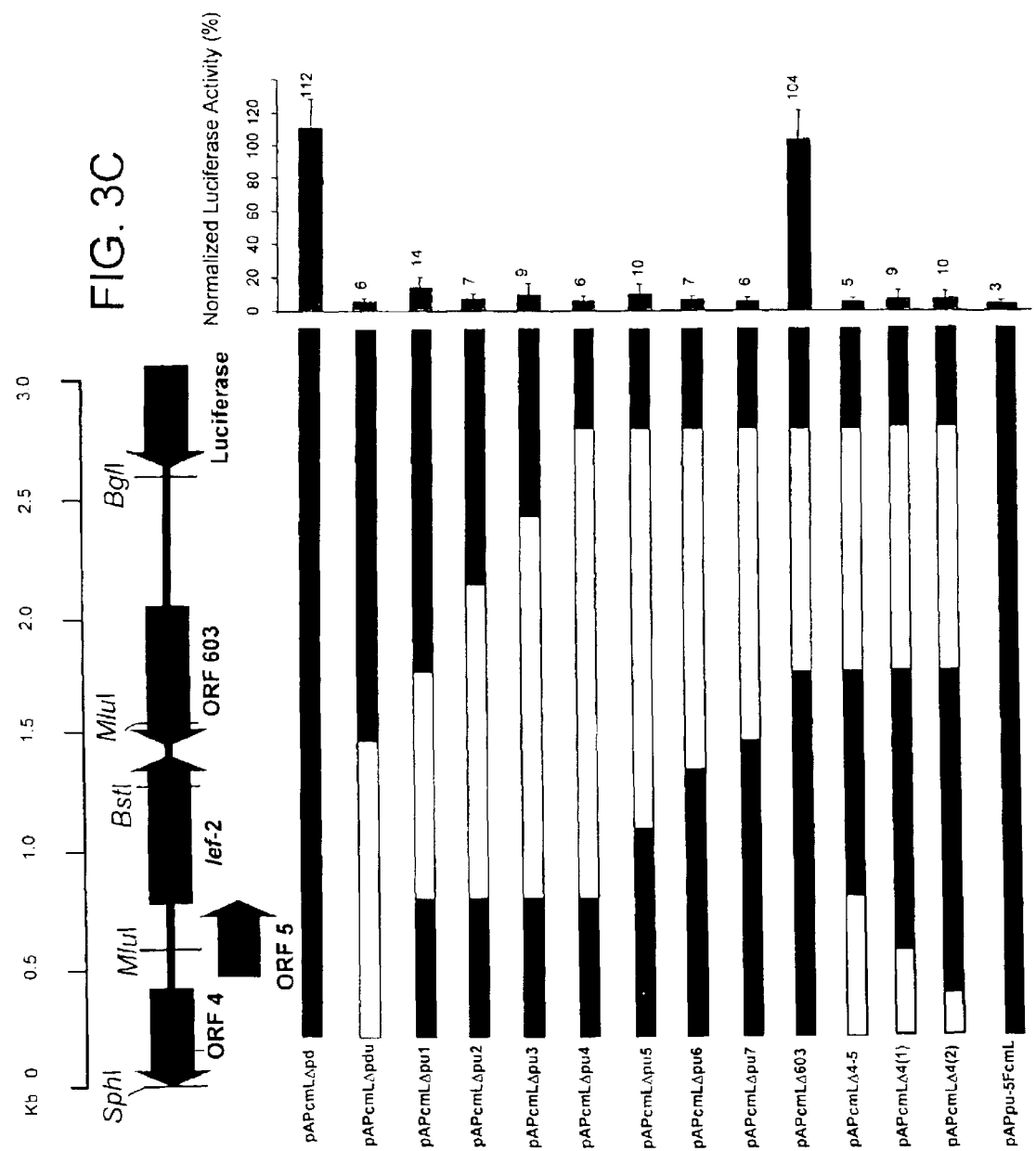

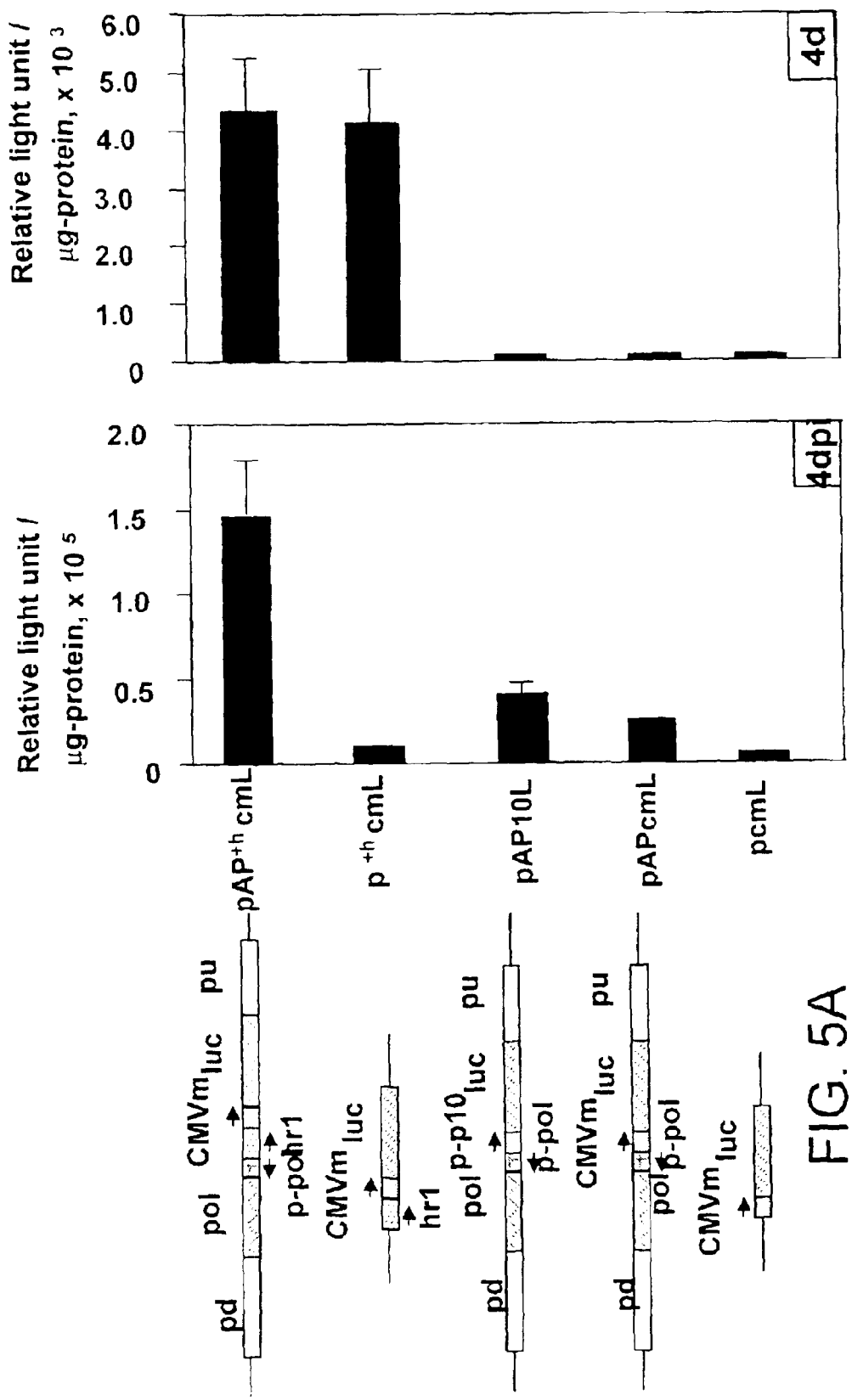

SEQUENCE LISTING

<160> NUMBER OF SEQ ID NOS: 4

<210> SEQ ID NO 1
<211> LENGTH: 456
<212> TYPE: DNA
<213> ORGANISM: Autographa californica

<400> SEQUENCE: 1

| | | | | | |
|---|---|---|---|---|---|
| atgaaactaa | cttacaagat | ggctagtttg | ttaaaatacg | cgctgcgctt | gactcgggaa | 60 |
| tacaaagaaa | acattattcc | acactttgat | cacttgactc | gattgcgcga | tttaatcgac | 120 |
| ggcatgatta | aaagcgagga | tgtacaacgt | tttaatcgca | ctaatcgcaa | tgatttaatt | 180 |
| tcggcttgca | tgcaaatcaa | cgttcggacg | tacatgccca | acgccacgat | agatatgcgc | 240 |
| aaacaaccca | actgtatata | ttttcgaatt | tgccaatatt | gccacttgga | ggccgacgtg | 300 |
| ccttcgcccg | acgatcattc | ggtgtacaga | tacttgtgcg | tcgcgtgcgg | cacgccgctg | 360 |
| gtcatcgacc | acccgctcga | cgtgttcggc | cacacggagg | aaggcgtcaa | cgaactgctc | 420 |
| gaggtgcagc | gagtcaacgc | gggcggggag | ttgtag | | | 456 |

<210> SEQ ID NO 2
<211> LENGTH: 321
<212> TYPE: DNA
<213> ORGANISM: Autographa californica

<400> SEQUENCE: 2

| | | | | | |
|---|---|---|---|---|---|
| atgtatcgca | cgtcaagaat | taacaatgcg | cccgttgtcg | catctcaaca | cgctatgata | 60 |
| gagatcaaat | aaagcgcgaa | ttaaatagct | tcgacgcaac | gtgcacgatc | gtgcacgcgt | 120 |
| tccggcacga | gctttgattg | taataagttt | tacgaagcga | tgacatgacc | ccgtagtgac | 180 |
| aacgatcacg | cccaaaagaa | ctgccgatac | aaaattaccg | agtatgcggt | gacgttaaaa | 240 |
| ctattaagcc | atccaatcga | ccgttgtcga | atcaggaccg | ctgggcgaga | agccgcgaag | 300 |
| tatggcgaat | gcatcgtata | a | | | | 321 |

<210> SEQ ID NO 3
<211> LENGTH: 633
<212> TYPE: DNA
<213> ORGANISM: Autographa californica

<400> SEQUENCE: 3

| | | | | | |
|---|---|---|---|---|---|
| atggcgaatg | catcgtataa | cgtgtggagt | ccgctcatta | gagcgtcatg | tttagacaag | 60 |
| aaagctacat | attttaattga | tcccgatgat | tttattgata | aattgaccct | aactccatac | 120 |
| acggtattct | acaatggcgg | ggttttggtc | aaaatttccg | gactgcgatt | gtacatgctg | 180 |
| ttaacggctc | cgcccactat | taatgaaatt | aaaaattcca | attttaaaaa | acgcagcaag | 240 |
| agaaacattt | gtatgaaaga | atgcgtagaa | ggaaagaaaa | atgtcgtcga | catgctgaac | 300 |
| aacaagatta | atatgcctcc | gtgtataaaa | aaaatattga | acgatttgaa | agaaaacaat | 360 |
| gtaccgcgcg | gcggtatgta | caggaagagg | tttatactaa | actgttacat | tgcaaacgtg | 420 |
| gtttcgtgtg | ccaagtgtga | aaaccgatgt | taatcaagg | ctctgacgca | tttctacaac | 480 |
| cacgactcca | agtgtgtggg | tgaagtcatg | catcttttaa | tcaaatccca | agatgtgtat | 540 |
| aaaccaccaa | actgccaaaa | aatgaaaact | gtcgacaagc | tctgtccgtt | tgctggcaac | 600 |
| tgcaagggtc | tcaatcctat | ttgtaattat | tga | | | 633 |

-continued

```
<210> SEQ ID NO 4
<211> LENGTH: 457
<212> TYPE: DNA
<213> ORGANISM: Autographa californica

<400> SEQUENCE: 4
gttttacaag tagaattcta cccgtaaagc gagtttagtt ttgaaaaaca aatgacatca        60
tttgtataat gacatcatcc cctgattgtg ttttacaagt agaattctat ccgtaaagcg       120
agttcagttt tgaaaacaaa tgagtcatac ctaaacacgt taataatctt ctgatatcag       180
cttatgactc aagttatgag ccgtgtgcaa aacatgagat aagtttatga catcatccac       240
tgatcgtgcg ttacaagtag aattctactc gtaaagccag ttcggttatg agccgtgtgc       300
aaaacatgac atcagcttat gactcatact tgattgtgtt ttacgcgtag aattctactc       360
gtaaagcgag ttcggttatg agccgtgtgc aaaacatgac atcagcttat gagtcataat       420
taatcgtgcg ttacaagtag aattctactc gtaaagc                                457
```

BACULOVIRUS ENHANCER-LIKE SEQUENCE

RELATED APPLICATIONS

This application claims the benefit of provisional application Ser. No. 60/305,513, filed Jul. 13, 2001, the contents of which are incorporated herein by reference in their entirety.

BACKGROUND

The baculoviruses comprise a group of viruses that contain circular double-stranded DNA genomes of 90–160 kb (Blissard and Rohrmann, 1990; King and Possee, 1994; Miller and Dawes, 1979; and Smith and Summers, 1979). The circular 131-kb DNA genome of *Autographa californica* nuclear polyhedrosis virus (AcMNPV) is composed almost entirely of unique DNA sequences, except for several small repeated sequences known as homologous regions (hrs) that are interspersed within the viral genome (Ayers et al., 1994; Cochran and Faulkner, 1983; and Guarino et al., 1986). These hr sequences have been found to be enhancers for early gene transcription (Guarino et al., 1986; and Guarino and Summers, 1986) and as origins of DNA replication (Kool et al., 1993; Pearson, 1992).

The baculovirus expression vector system is one of the most popular systems for exogenous proteins production. Recombiannt proteins are expressed to very high levels due to the control of two very late polyhedrin and p10 promoters (Hasnain et al., 1997; Lopez-Ferber et al., 1995). However, the cell machinery critical for post-translational processing (e.g., glycosylation) is generally deteriorated during late and very late phases of baculovirus infection. Therefore, using early promoters for recombinant protein expression is an alternative approach to improve protein quality (Jarvis et al., 1990; and Jarvis et al., 1996). However, the activity of these early promoters is low compared with that of the very late promoters polyhedrin or p10.

SUMMARY

The invention is based, in part, on the discovery of an enhancer-like sequence upstream from the polyhedrin gene locus in the genome of baculovirus. This sequence, named herein "pu" was unexpectedly found to strongly activate the expression of a foreign gene early after viral infection, making pu very useful for the expression of recombinant proteins in insect cells with or without recombinant baculovirus. This pu sequence contains at least three open reading frames (ORFs) and can enhance the expression of full or minimal promoters. The ORFs contained in the pu sequence are ORF4 (SEQ ID NO:1), ORF5 (SEQ ID NO:2), and lef2 (SEQ ID NO:3). The pu sequence enhanced the expression of viral and cellular promoters to a much greater extent than the p10promoter. In addition, the pu sequence can act synergistically with the baculovirus hr sequence to enhance expression to surprisingly high levels.

Accordingly, in one aspect the invention features a nucleic acid construct, e.g., a plasmid construct or a viral construct (e.g., a baculovirus-based construct), useful for the high level expression of a heterologous protein in a cell, e.g., an insect cell. The construct includes a nucleotide sequence of less than 10,000 nucleotides, for example less than 5000 nucleotides, less than 2500 nucleotides, e.g., about 1500 nuclcotides, which sequence includes the sequences shown as SEQ ID NO:1, SEQ ID NO:2 and SEQ ID NO:3 and can enhance the activity of an operably linked promoter. A non-limiting example of such a nucleotide sequence is the pu sequence described herein. It is understood that a limited number of additional nucleotides at the 5' and/or 3' end of the pu sequence would not interfere with the pu sequence's enhancer like activity. The enhancer like sequence is operably linked to a promoter, e.g., a cellular promoter, e.g., an insect cell promoter, or a viral promoter, which promoter is operably linked to a heterologous coding sequence in the constructs described herein. As the invention is not intended to encompass the enhancer-like sequence as it occurs in the naturally occurring baculovirus genome, the 5' and/or 3' sequence immediately flanking the nucleotide sequence that includes SEQ ID NO:1, SEQ ID NO:2 and SEQ ID NO:3 in the construct is different from the 5' or 3' sequence immediately flanking the sequence in a naturally occurring AcMNPV genome. In some embodiments, the constructs described herein also include a baculovirus hr sequence, e.g., the sequence shown as SEQ ID NO:4 or another hr sequence, e.g., as described in Ayres et al. (1994. Virology 202, 586–605). The hr sequence can operate cooperatively with the enhancer-like sequence described herein to produce unexpectedly high levels of expression from a promoter.

The constructs described herein can be used to express any heterologous coding sequence. As used herein, a "heterologous coding sequence" means that the coding sequence is not associated in nature with the promoter to which it is linked in the constructs of the invention. The heterologous coding sequence can be a non-viral coding sequence, e.g., an insect or mammalian coding sequence, e.g., a human coding sequence. Coding sequences that can usefully be used in the constructs described herein include, but are not limited to, sequences encoding enzymes, vaccines, antibodies, biologically active peptides, tumor antigens, or surface antigens. Nonlimiting examples of such sequences that can be expressed in a baculovirus system are described in, e.g., Huang et al. (2001) J Gen Virol 82:1767–76; Treanor et al. (2001) Vaccine19:1732–7; Lieby et al. (2001) Blood 97:3820–8; Myles et al. (2001) Biochem J 357:225–32; tumor antigen: Soares et al.(2001) Protein Expr Purif 22:92–100; Fukumoto et al. (2001) J Clin Microbiol 39:2603–9.

The coding sequence is under the control of a viral or insect promoter, e.g., a minimal CMV promoter, a p35 promoter, a heat shock promoter, a p10 promoter, or a polyhedrin promoter, which promoters are known in the art. The promoter can be other than a polyhedrin promoter.

A construct described herein can also include one or more additional sequences necessary for expression of the heterologous coding sequence. For example, a construct described herein can include, e.g., a selectable marker, a 3' untranslated sequence (UTS), a polyadenylation site, a foreign origin of replication e.g., a human origin of replication (described, e.g., in Burhans et al., 1994, Science 263: 639–640), or Epstein-Barr Virus replication origin and transacting factor. Such foreign origins of replication can increase gene expression in human cells. The constructs described herein can be made using standard molecular biology techniques, e.g., as described in Sambrook et al. Molecular Cloning: A Laboratory Manual, 3d ed., 2001, Cold Spring Harbor, which is hereby incorporated in its entirety.

In another aspect, the invention features a method of producing a polypeptide. The method includes: providing a nucleic acid construct described herein, e.g., a plasmid or viral construct described herein; introducing the nucleic acid construct into a cell, e.g., an insect cell; and allowing the cell to express a polypeptide encoded by the coding sequence.

In some embodiments, the nucleic acid construct is introduced into the cell by infection with a virus, e.g., a baculovirus, containing the nucleic acid construct.

In another embodiment, the nucleic acid construct is a plasmid construct. When the nucleic acid construct is a plasmid construct, the method can include the step of co-infecting the cell with a baculovirus.

In another aspect, the invention features a host cell, e.g., an insect cell, containing a nucleic acid construct described herein. Procedures for introducing constructs, e.g., baculovirus constructs, into cells, e.g., insect cells, are known in the art. See, e.g., Pfeifer et al., 1997, Gene 188:183–190; and Clem et al., 1994, J Virol 68:6759–6762.

A "nucleic acid construct" is defined herein as a nucleic acid molecule that has been modified to contain segments of nucleic acid that are combined and juxtaposed in a manner that would not otherwise exist in nature. The term encompasses plasmid and viral constructs.

The term "operably linked" is defined herein as a configuration in which a first sequence (generally a regulatory sequence) is placed at a position relative to a second sequence, e.g., a coding sequence or another control sequence, such that the first sequence affects the expression or activity of the second sequence. For example, a promoter can be operably linked to a coding sequence; an enhancer or enhancer-like sequence can be operably linked to a promoter. Sequences that are operably linked can be, but need not be, adjacent to each other.

DESCRIPTION OF THE FIGURES

FIG. 5. (Parts A–C) Activation of the CMVm promoter by pu and hr sequences with or without viral co-infection. (A) Map of constructs for luciferase expression. (B) Luciferase expression by the transfection of individual constructs with virus co-infection. (C) Luciferase expression by the transfection of individual constructs without virus co-infection. "+" represents hr sequence with positive orientation.

DETAILED DESCRIPTION

Figure 1:
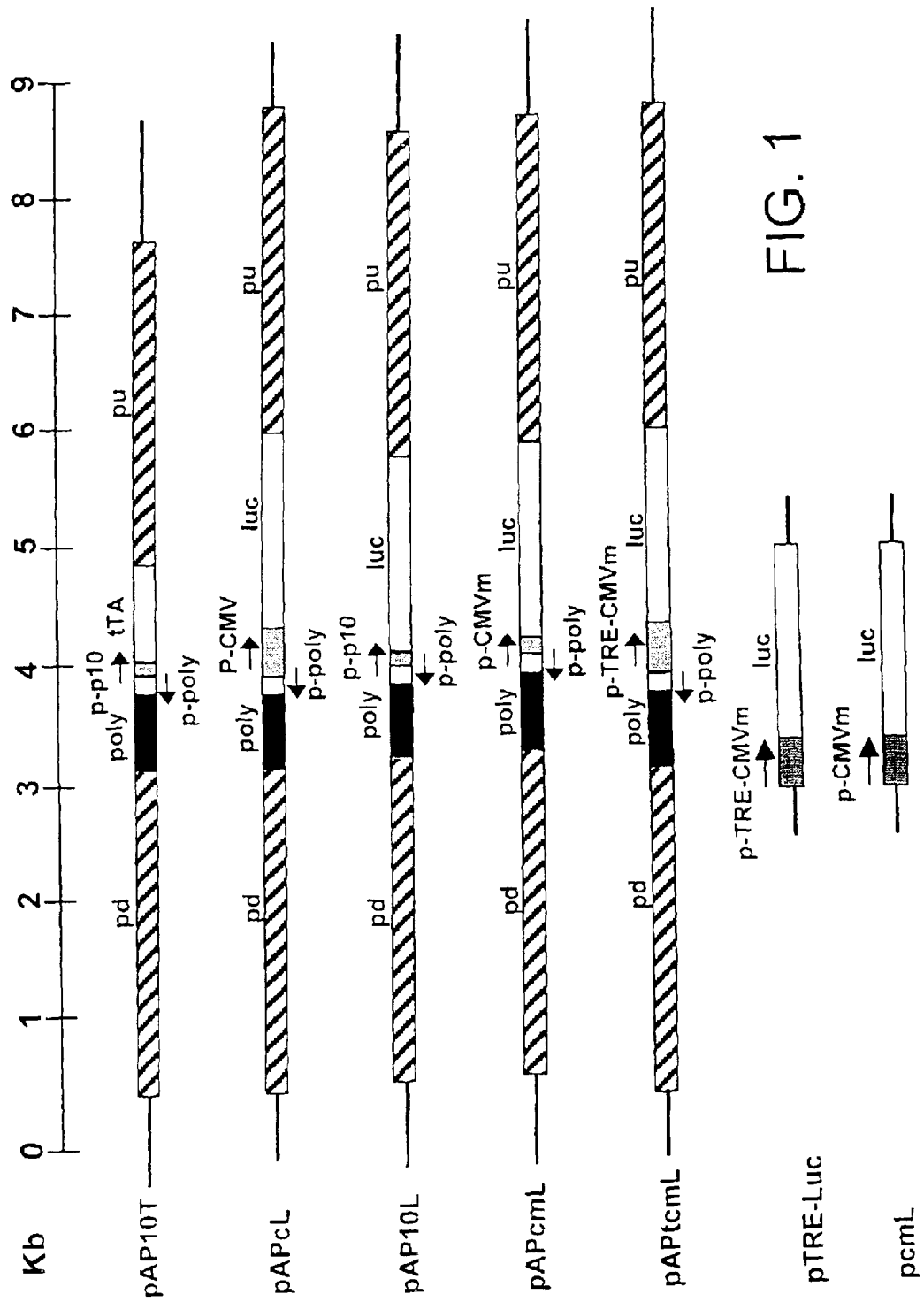
FIG. 1. Plasmids containing different promoter constructs for the expression of luciferase. Different promoter constructs were used to drive luciferase in plasmid pAcUW21 (PharMinging). Promoters used included the full CMV promoter (p-CMV), they p promoter (p-p10) of AcMNPV, the minimal CMV promoter (p-CMVm), and the TRE element fused to CMVm (p-TRE-CMVm). All of these constructs are located upstream from the polyhedrin gene.

A novel baculovirus enhancer-like element is described herein that can strongly activate the activity of full or minimal promoters, e.g., the minimal CMV promoter, or the p35 promoter, in insect cells. The enhancer like element (e.g., the pu region described herein) includes the ORF4, ORF5, and lef2 sequences, the three of which are required and sufficient for strong activation of a promoter. In cis linkage of the enhancer-like element with a promoter is necessary for the activation of the target promoter. The activity of the enhancer-like element is position-independent. In addition, the enhancer-like element and baculovirus hr sequence together function synergistically to reach a surprisingly high expression level from a promoter. The combined enhancer activity is not only very strong, but is also expressed very early.

The pu sequence contains three ORFs: lef2, ORF4 and ORF5. The individual ORFs lef2, ORF4 and ORF5 have been described elsewhere. Lef2 has been described by Passarelli and Miller, 1993, JV 67:2149–2158; Lu and Miller, 1995, JV 69:975–982; and Todd et al., 1995, JV 69: 968–974. The data described herein shows that omission of lef2 abolishes the function of the pu sequence (FIG. 3C), but the presence of the lef2 gene or its ORF alone does not have enhancer activity by itself. Co-infection of wild type AcMNPV, which provides lef2 gene products in trans, did not enhance minimal CMV promoter activity in a plasmid unless it contained the entire pu sequence (FIG. 3C). Thus, lef2 alone is not sufficient for the activation of CMVm promoter.

ORF 4 is a putative viral ORF whose function is not well characterized (Ayres et al., 1994). ORF 5 does not seem to be essential for the life cycle of baculovirus, because its truncation supports late and very late gene expression (Passarelli and Miller, 1993). However, results from the transfection of the plasmids pApu5FcmL (FIG. 3C) revealed that the mutation of this ORF abolishes high level expression of the CMVm promoter. The presence of three ORFs in the pu sequence suggests that protein products derived from this region may also play a role in the activation of target promoters.

SEQ ID NO:1 (ORF4)
ATGAAACTAACTTACAAGATGGCTAGTTTGTTA-
AAATACGCGCTGCGCTTGACTCGGGAATACAA
AGAAAACATTATTCCACACTTTGATCACTTGAC
TCGATTGCGCGATTTAATCGACGGCATGATTA
AAAGCGAGGATGTACAACGTTTTAATCG-
CACTAATCGCAATGATTTAATTTCGGCT-
TGCATGCAAATCAACGTTCGGACG-
TACATGCCCAACGCCACGATAGATATGCGCAA-
ACAACCCAACTGTATATA TTTTCGAATTTGC-
CAATATTGCCACTTGGAGGCCGACGTGC-
CTTCGCCCGACGATCATTCGGTGT ACAGA-
TACTTGTGCGTCGCGTGCGGCACGC-
CGCTGGTCATCGACCACCCGCTCGACGT-
GTTCGGC CACACGGAGGAAGGCGTC-
AACGAACTGCTCGAGGTGCAGCGAGTCAACG-
CGGGCGGGGAGTTGTA G

SEQ ID NO:2 (ORF5)
ATGTATCGCACGTCAACAATTAACAAT-
GCGCCCGTTGTCGCATCTCAACACGC-
TATGATAGAGAT CAAATAAAGCGCGA-
ATTAAATAGCTTCGACGCAACGTGCACGATCG-
TGCACGCGTTCCGGCACGA GCTTTGATTG-
TAATAAGTTTTACGAAGCGATGACAT-
GACCCCGTAGTGACAACGATCACGCCCAA
AAGAACTGCCGATACAAAATTACCGAG-
TATGCGGTGACGTTAAAACTATTAAGC-
CATCCAATCGA CCGTTGTCGAATCAGGAC-
CGCTGGGCGAGAAGCCGCGAAGTATGGCGAA-
TGCATCGTATAA

SEQ ID NO:3 (LEF2)
ATGGCGAATGCATCGTATAACGTGTGGAGT-
CCGCTCATTAGAGCGTCATGTTTAGA-
CAAGAAAGC TACATATTTAATTGATCCCGAT-
GATTTTATTGATAAATTGACCCTAACTC-
CATACACGGTATTCT ACAATGGCG-
GGGTTTTGGTCAAAATTTCCGGACTGC-
GATTGTACATGCTGTTAACGGCTCCGCCC
ACTATTAATGAAATTAAAAATTCCAATTTTAAA-
AAACGCAGCAAGAGAAACATTTGTATGA-
AAGA ATGCGTAGAAGGAAAGAAAAAT-
GTCGTCGACATGCTGAACAACAAGAT-
TAATATGCCTCCGTGTA TAAAAAAAATATT-
GAACGATTTGAAAGAAAACAATGTACCGCG-
CGGCGGTATGTACAGGAAGAGG TTTATACT-
AAACTGTTACATTGCAAACGTGGTTTCGT-
GTGCCAAGTGTGAAAACCGATGTTTAAT
CAAGGCTCTGACGCATTTCTACAACCAC-
GACTCCAAGTGTGTGGGTGAAGTCATG-
CATCTTTTAA TCAAATCCCAAGATG-
TGTATAAA CCACCAAACTGCCAAAAAAT-
GAAAACTGTCGACAAGCTCTGT CCGTTT-
GCTGGCAACTGCAAGGGTCTCAATC-
CTATTTGTAATTATTGA

SEQ ID NO:4 (hr)
GTTTTACAAGTAGAATTCTACCCGTAAA-
GCGAGTTTAGTTTTGAAAAACAAATGA-
CATCATTTGT ATAATGACATCATCCCCTGAT-
TGTGTTTTACAAGTAGAATTCTATCCG-
TAAAGCGAGTTCAGTTT TGAAAACA-
AATGAGTCATACCTAAACACGTTAATAATCT-
TCTGATATCAGCTTATGACTCAAGTT ATGAGC-
CGTGTGCAAAACATGAGATAAGTTTAT-
GACATCATCCACTGATCGTGCGTTACAAGTAG
AATTCTACTCGTAAAGCCAGTTCGGT-
TATGAGCCGTGTGCAAAACATGACAT-
CAGCTTATGACTC ATACTTGATTGTGTTT-
TACGCGTAGAATTCTACTCGTAAAGCGAGTTC-
GGTTATGAGCCGTGTGC AAAACATGA-
CATCAGCTTATGAGTCATAATTAATCGTGCGTT-
ACAAGTAGAATTCTACTCGTAAA GC

EXAMPLES

Example 1

Cell Cultures and Viruses

The S. frugiperda IPLB-Sf21 (Sf21) cell line was cultured as monolayers in TNM-FH insect medium containing 8% heat-inactivated fetal bovine serum (Lee et al., 1998; Lin et al., 1999). These cells used for propagation and infection of wild type AcMNPV. All viral stocks were prepared and titered according to the standard protocol described by O'Reilly et al. (1992).

Example 2

Plasmid Transfection for Transient Assay of Promoter Activities

Plasmids tested for expression of protein tTA or luciferase were transfected into $4 \times 10^4$ Sf21 cells seeded in wells of a 96-well plate. 0.1 mg of each plasmid was transfected using 0.5 mg of lipofectin (Life Technologies, Inc.) per well in 50 ml of serum-free TNM-FH according to the protocol provided by the manufacturer. After transfection for 8–14 hours at 27° C., the transfection medium was removed and replaced with 100 ml of TNM-FH medium containing 8% heat-inactivated fetal bovine serum. After incubation at 27° C. for 24 hours, wild type AcMNPV at an m.o.i. of 1 was added into Sf21 cells to assist the proper expression of the transfected promoters. Luciferase activity was assayed three days after infection. Each sample was performed in triplicate or four replicates.

Example 3

Luciferase Activity Assay

Cells of each well were lysed for 10 min. in 100 ml CCLR (Culture Cell Lysis Reagent) containing 100 mM potassium phosphate (pH 7.8), 1 mM EDTA, 10% glycerol, 1% Triton X-100, and 7 mM β-mercaptoethanol. After centrifugation at 14,000 rpm for 10 min., the lysate supernatant (5 ml to 50 ml) was incubated in 180 ml of LAR (Luciferase Assay Reagent) containing 25 mM tricine (pH 7.8), 15 mM potassium phosphate (pH 7.8), 15 mM $MgSO_4$, 4 mM EGTA, 1 mM ATP, and 0.1 mM DTT. 50 ml of 0.2 mM luciferin (Promega) solution was auto-injected and the relative light units (RLU) were measured by a luminometer (Berthold, Lumat LB 9501). The concentration of total protein in cell lysate was determined using the Coomassieâ protein assay reagent kit (PIERCE). Data (means±standard deviations)

were collected from triplicate assays of three independent transfection or viral infection experiments.

Example 4

Construction of Plasmids

A. Plasmids containing CMVm and p10 Promoters.

Figure 3A:
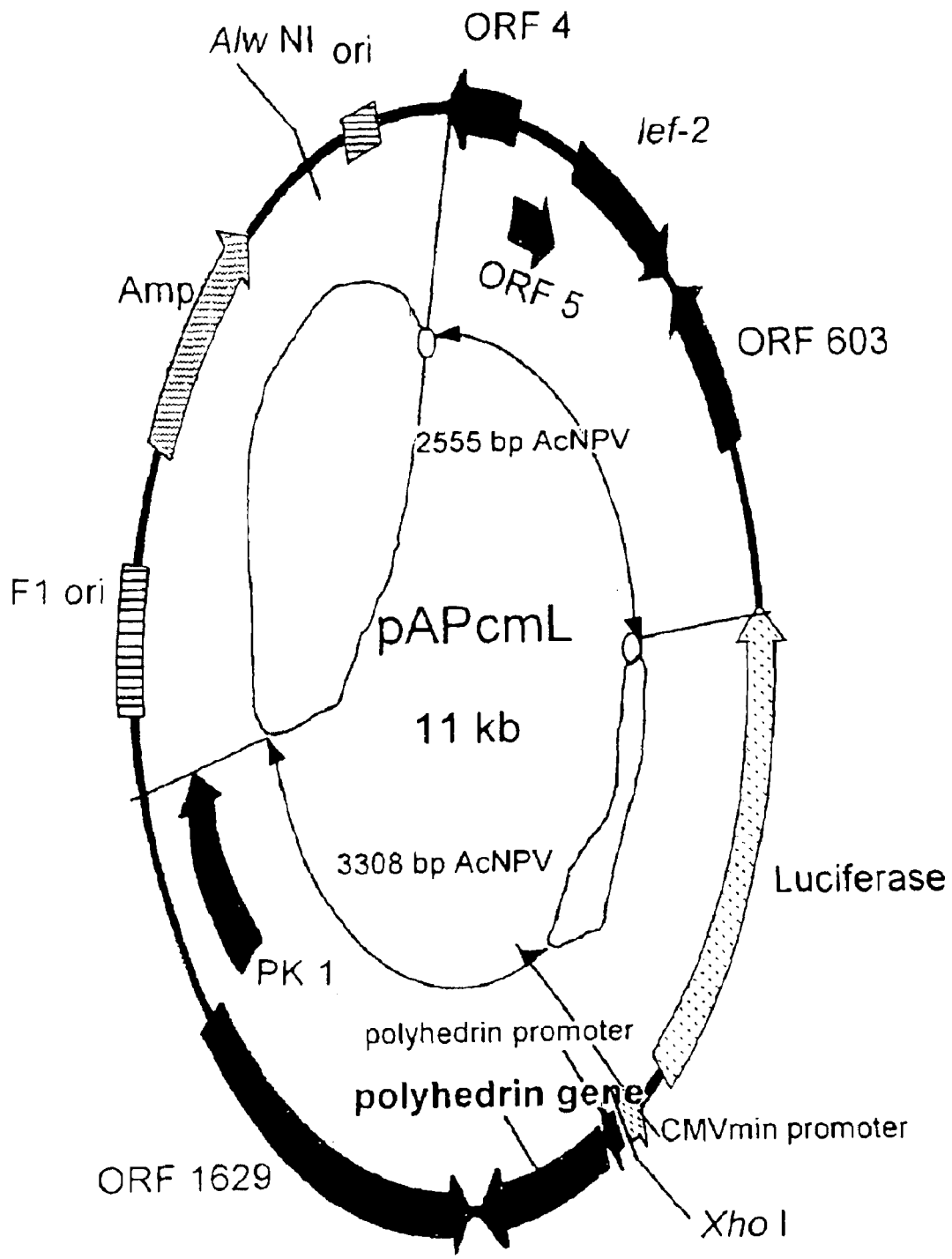
FIG. 3. (Parts A–C) Characterization of the region responsible for the activation of the CMVm promoter in baculovirus/insect cells systems. (A) Viral genes and ORFs contained in the original plasmid pAPcmL are shown. (B) and (C) Analysis of luciferase expression in plasmids with various deletions. In each panel, maps of the deleted (blank bar) and remaining sequences (filled bar) of plasmid pAPcmL are shown on the left, Normalized luciferase activities expressed by these clones are shown on the right. (B) pAPcmLΔpd is a construct with the complete deletion of the polyhedrin downstream sequence (pd), and pAPcmLΔPdu is the construct with the complete deletion of polyhedrin upstream (pu) and partial of downstream sequences. (C) Deletion analysis of the (pu) region. pAPcmLΔpu1-Δpu7 are seven pu-deleted constructs; pAPcmLΔ603 is the construct with ORF 603 deletion only; pAPcmLΔ4-5 is a construct with both ORF 4 and ORF 5 deletions in addition to deletion of ORF 603; pAPcmLΔ4 (1)-Δ4(2) are two constructs with partial deletion of ORF 4 in addition to deletion of ORF 603.

Deletion constructs are shown in the various figures together with their activity assays. All PCR products were confirmed by DNA sequence analysis. The CMVm and TRE-CMVm promoters were originally constructed by Gossen and Bujard (1992). The CMVm promoter encompasses the sequence between +75 and −53 of the CMV promoter, and the TRE-CMVm promoter contains seven copies of the 42-bp tetO sequence derived from operator O2 of Tn10 that are fused to the CMVm promoter (Gossen and Bujard, 1992, FIG. 1). The luciferase coding sequence from the pTRE-Luc plasmid (positions 507 to 2187 bp, ClonTech) was driven by CMVm or TRE-CMVm promoters,which were inserted separately into pAcUW21 (Pharmingen) to replace the p10 promoter originally located in this plasmid. The resulting plasmids were named pAPcmL and pAPcmL, respectively (FIG. 3A and FIG. 1). The same luciferase coding sequence from the pTRE-Luc plasmid was also cloned into pAcUW21 under the control of the p10 promoter of AcMNPV in the plasmid pAcUW21, and the resulting plasmid was named pAP10L (FIG. 1). The full-length CMV promoter derived from pTet-Off (from position 68 to 673 bp, ClonTech) together with the luciferase coding region were inserted into pAcUW21 in replace of the p10 promoter, and the resulting plasmid was named pAPcL (FIG. 1). The coding region of the transactivator protein tTA from plasmid pTet-Off (ClonTech) was cloned into pAcUW21 under control of the p10 promoter and the resulting plasmid was named pAP10T (FIG. 1).

B. Deletion Constructs.

Figure 3B:
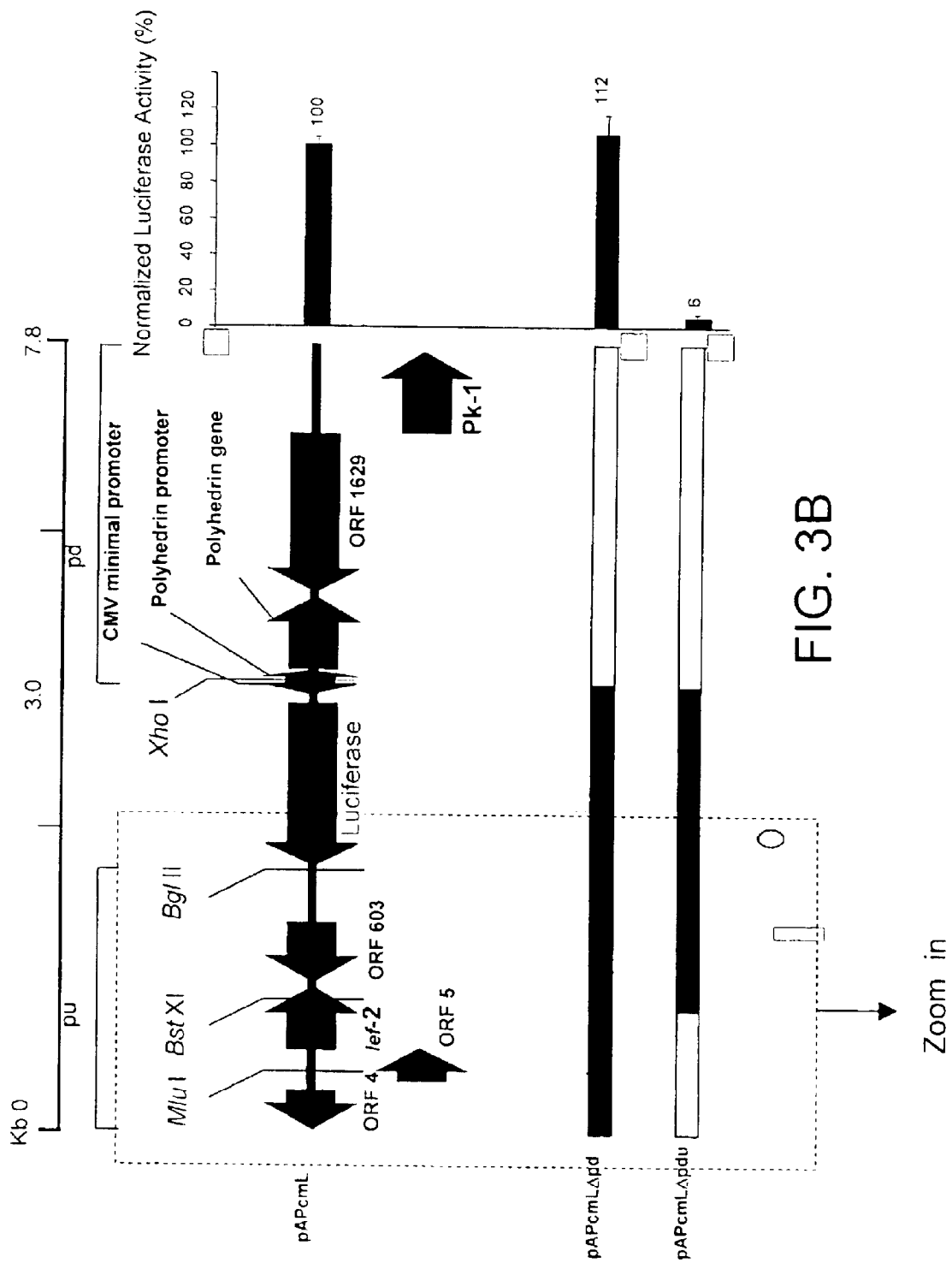

Polyhedrin gene (polh) downstream sequences (designated as Pd) were deleted from plasmid pAPcmL (FIG. 3A) and the resulting plasmid was named pAPcmLDPd. Plasmid pAPcmLDPd was generated by first digesting pAPcmL with AlwNI, blunt-ending with T4 DNA polymerase, and then cutting with XhoI (FIG. 3A). The resulting fragment was subcloned into XhoI-SmaI-digested plasmid pBluescript (pBSKSM+, Stratagene). Plasmid pAPcmLDPdu contains only partial polh upstream sequences. This deletion construct was obtained by digesting pAPcmL with BstXI, blunt-ending with T4 DNA polymerase, then further digesting with XhoI, and followed by sub cloning this BstXI-XhoI-digested fragment into XhoI-SmaI-digested pBSKSM+(FIG. 3B).

Plasmids pAPcmLDpu1 to pAPcmLDpu7 were constructed for deletion analysis of the pu region (FIG. 3C). The pAPcmLDpu1 was made by MluI digestion and followed with self-ligation of pAPcmL. pAPcmLDpu2 and pAPcmLDpu3 were generated by cutting pAPcmL with MluI and BglII, and then ligating respectively with a 5'-MluI/3'-BglII PCR-amplified product containing pAPcmL regions 1877–2562 nt and 2218–2562 nt (FIG. 3A). Plasmid pAPcmLDpu4 was constructed by cutting pAPcmL with MluI and BglII, blunt-ending with T4 DNA polymerase, and religating with T4 DNA ligase. To generate pAPcmLDpu5 and pAPcmLDpu6, pAPcmL was digested with MluI and BglII, and respectively ligated with the 5'-MluI/3'-BglII PCR-amplified product containing pAPcmL regions 546–1198 nt and 546–883 nt (FIG. 3A). Plasmid pAPcmLDpu7 was constructed by digesting pAPcmL with BstXI and BglII, blunt-ending with T4 DNA polymerase, and re-ligating with T4 DNA ligase. The ORF 603 deletion construct pAPcmLD603 was generated by partial digestion of pAPcmL with MluI and complete digestion with BglII, blunt-ending, and religation. Plasmid pAPcmLr4–5 was produced from pAPcmLrPd first by MluI partial digestion and BglII complete digestion, blunt-ending, and religation. The derived plasmid (pBSKcmL) containing no ORF 603 was further digested with NotI (in mutiple cloning sites at the 3' end of ORF4) and MluI, blunt-ended with T4 DNA polymerase, and relegated, resulting in deletion of ORF 4 and part of the 5' end of ORF 5. 3¢-MluI and 5¢-blunt ends were introduced into two PCR-generated fragments from pAPcmL containing 377–626 nt and 183–626 nt (FIG. 3A). Subcloning them into NotI/blunt-ending and MluI-digested pBSKcmL produced ORF 4 deletion constructs pAPcmLr4(1) and pAPcmLr4(2), respectively.

C. Construction of Plasmids Containing the pu Fragment Up- and Down-stream from the CMVm Promoter.

All plasmids described in this paragraph are listed in FIG. 3. Fragment cmL was derived from pTRE-Luc (Clontech) containing only the CMVm promoter and a luciferase coding sequence (FIG. 3). The symbol (+) and (−) represents that the pu fragment is located downstream or upstream, respectively, to the CMVm promoter. To produce pApu(+) cmL (FIG. 4A), pAPcmLΔ603 (see FIG. 3C) was digested with AlwNI, blunt-ended, and then cut with XhoI (see FIG. 2A for AlwNI and XhoI sites). The resulting fragment was subcloned into XhoI-SmaI-digested pBSKSM+. pApu(−) cmL (FIG. 4A) was generated by inserting a 5¢-AatII/3¢-XhoI pu fragment amplified by PCR containing the full-length ORF 4, ORF 5, and lef-2 into AatII-XhoI-digested pcmL (FIG. 1).

D. Plasmids Containing the Luciferase Gene Driven by CMVm, p35, and hsp70 Promoters.

All plasmids constructed as described below are listed in FIG. 8. Plasmid phL was contructed from pTRE-Luc (Clontech) by removing a 0.47-kb XhoI-BamHI fragment containing the tet operators and the CMVm promoter and replacing it with a hsp70 promoter from pKih35hN (Lee et al., 1998). A 0.53-kb fragment carrying the XhoI site at both ends was generated from AcMNPV genomic DNA by PCR. This fragment contains a 457-bp hr1 region (Ayres et al., 1994). The fragment was blunt-ended and ligated into the blunt-end treated NotI site in front of the hsp70 promoter in phL to generate phhL. Primers 5' of hr1 and 3' of SV40 poly(A) of the luc gene in phhL were used to generate a blunt-ended PCR product containing hr1-hsp70-luc of 3.67 kb. The product was ligated into pCR-Blunt (Invitrogen) to generate an intermediate plasmid pCRhhL, from which the fragment containing hr1-hsp70-luc was obtained by digestion, and then blunt-end treated and ligated into pAcUW21 (Pharmingen) to generate pAPhhL.

Plasmid phcmL was constructed as described below. The XhoI-digested hr1 PCR fragment was cloned into pcmL to generate phcmL. Using PCR, a fragment containing hr1-CMVm promoter-luc was produced from phcmL and ligated into pAPtcmL, which had been digested by XhoI and EcoRV to remove the tet operators, the CMVm promoter, and the luc gene. This resulted in pAPhcmL.

Plasmid p35mL was constructed by megaprimer PCR technique (Barik 1997). Two primers were designed to amplify a 80-bp PCR fragment from AcMNPV genomic DNA by PCR. A roughly 40 bp long 3' primer, its 5' end contains a sequence complementary to the 5' region of luc ORF. The resulted 80-bp PCR fragment was purified by electroelution into a dialysis bag (Sambrook et al., 1989). This fragment contains a 45-bp AcMNPV p35 basal promoter (Rodems and Friesen, 1993) and is used as the 5' primer (megaprimer) to amplify the luc gene from pTRE-Luc. The final PCR product consists of both the p35 basal promoter and the luc gene and was cloned into pCR-Blunt vector to yield p35mL. The XhoI-digested hr1 fragment was cloned into the XhoI site in front of the p35 minimal promoter to yield ph35mL. A fragment containing hr1, the p35 minimal promoter, and the luc gene was obtained from ph35mL by ApaI digestion, and then blunt-ended and cloned into pAcUW21 to generate pAPh35mL.

A fragment of 1.57 kb containing the tTA coding region was generated from pTet-Off (Clontech) by PCR. It was ligated into pBSKSM+together with a fragment containing the hsp70 promoter to yield pKS/hT. A fragment containing hsp70 promoter-tTA from this plasmid was obtained by digestion, and was then blunt-ended and ligated into pAcUW21 to become pAPhT. The hr1 fragment was cloned into the blunt-end treated NotI site in front of the hsp70 promoter of pKS/hT to yield pKS/hhT. A fragment containing hr1-hsp70-tTA was digested from this plasmid, blunt-ended, and ligated into pAcUW21 to become pAPhhT.

To replace luc with the tTA coding region in phcmL, the plasmid was digested with PstI and ClaI digestion to remove part of the 5' region of the luc gene. A fragment containing tTA, obtained from pKS/hT by the same restriction digestion, was cloned into PstI/ClaI-digested phcmL resulting in the intermediate plasmid phcmTL. Using PCR, a fragment containing only hr1, the CMVm promoter, and tTA was obtained from this plasmid and cloned into pCR-Blunt to yield pCRhcmT. The same fragment was obtained again from pCRhcmT by digestion and blunt-end treatment, and was then ligated into pAcUW21 to result in pAPhcmT. All PCR-generated fragments mentioned above were verified by sequencing.

Example 5

Characterization of pu Region

A. A Sequence Upstream of the Polyhedrin Gene (pu) has Enhancer Activity

In the present study, the baculovirus transfer plasmid pAcUW21 (Pharmingen, Inc.) was the primary plasmid used for further contructions. This plasmid contains an intact polyhedrin gene and a p10 promoter; both the gene and the promoter are sandwiched between lateral DNA fragments adjacent to the polyhedrin gene of the baculovirus. In FIG. 1, plasmid pAcUW21 was used to insert a luciferase-coding region, driven by CMV, p10, CMVm, and tetO-CMVm promoters to result in plasmids pAPcL, pAP10L, pAPcmL, and pAPtcmL, respectively. The resultant viruses were termed vAPcL, VAP10 L, vAPcmL, and vAPtcmL, respectively. The promoter p10 was also used to drive tTA resulting in plasmid pAP10 T and virus vAP10T, separately. Finally, plasmid pTRE-Luc (Clontech.) was used as a necessary control. This is a plasmid that lacks any baculovirus sequence and the luciferase is driven by the tetO-CMVm promoter.

Figure 2A:
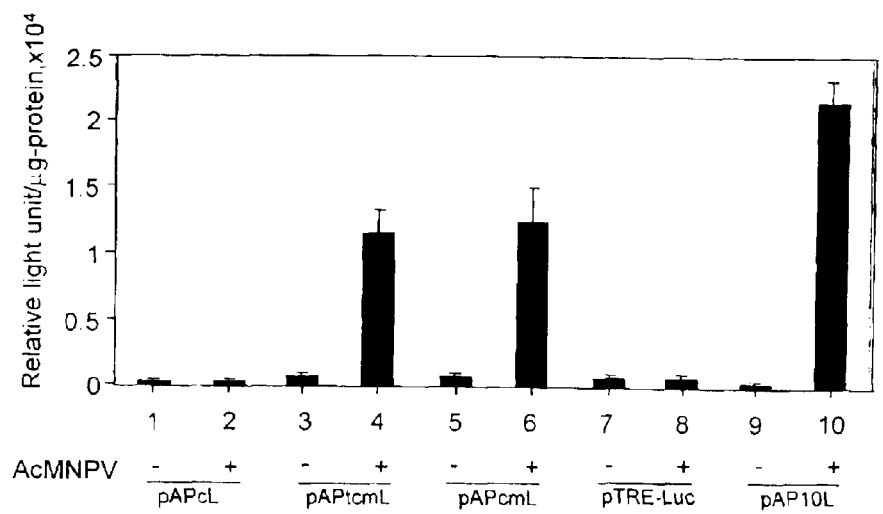
FIG. 2. (Parts A–C) Promoter activity assay by plasmid transfection. (A) Luciferase activity assay by the transfection of different plasmid constructs with or without viral co-infection. (B) Luciferase activity assay by the infection of different recombinant viruses. (C) Luciferase activity assay by the infection of recombinant virus vAPtcmL. The tTA-producing virus vAP10T and tetracycline (Tc) were added in some of the experiments to test whether the expression of luciferase by vAPtcmL can be controlled by tTA or tetracycline.
Figure 2B:
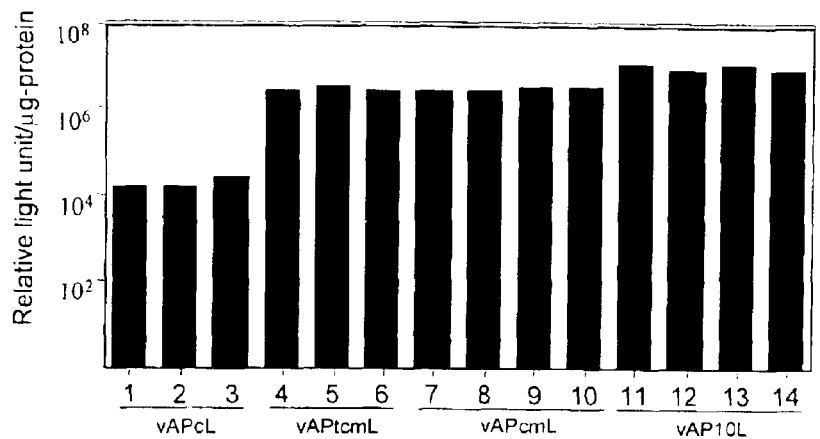
Figure 2C:

Previously, we showed that the luciferase activity is extremely low when pTRE-Luc is transfected into insect cells, but that it can be strongly stimulated by coinfection with vAP10T (Wu et al., 2000). However, we found that insertion of the tetO-CMVm promoter into plasmid pAcUW21, which in plasmid pAPtcmL (FIG. 1), caused activation of luciferase without the stimulation of tTA. More interestingly, luciferase activity was further highly stimulated upon the co-infection of wild type AcMNPV (FIG. 2A). Viral stimulation of luciferase expression remained in the transfection of plasmid pAPcmL into cells (FIG. 2A). The only difference between plasmids pAPtcmL and pAPcmL is the omission of the tetO sequence in plasmid pAPcmL (FIG. 1). These experiments showed that a short CMVm promoter sequence (in pAPcmL) can give rise to strong luciferase expression in the presence of baculovirus lateral fragments surrounding the polyhedrin promoter. A longer sequence containing the full length CMV promoter (in pAPcL) contrarily blocks luciferase's high level expression, while the tre element did not influence luciferase expression by the CMVm promoter (in pAPtcmL, FIG. 2B, C). In addition to not being expressed by plasmid transfection (FIG. 2A), the full length CMV promoter is also only weakly expressed by infection of recombinant baculovirus, regardless of the presence of the same baculovirus lateral fragments (FIG. 2B). Thus, the viral activation of luciferase expression is CMVm promoter specific and requires that baculovirus lateral DNA fragments surround the polyhedrin gene (FIGS. 1, 2).

To identify the viral DNA sequences responsible for the activation of minimal CMV promoter, viral lateral fragments appearing in the transfer vector were deleted separately using convenient sites. To investigate the role of specific baculovirus genes or sequences in the activation of CMVm promoter activity in baculoviruses, two deletion plasmids were first constructed. The polyhedrin and down stream genes were deleted resulting in pAPcmLΔpd; and another deletion construct, pAPcmLΔpdu, further deleted all or part of ORF4, ORF5, and lef2. The luciferase activity in cells transfected with pAPcmL followed by AcMNPV infection was used to normalize luciferase activity (as 100%) of other deleted plasmid constructs. Luciferase activity remained high in the transfection of plasmid pAPcmLΔpd, suggesting that the pd sequence is not critical for the activation of the CMVm promoter (FIG. 3B), While the construct pAPcmLΔpdu failed to support high luciferase expression (FIG. 3B). Therefore, the viral sequence upstream to the polyhedrin gene is responsible for the activation of CMVm and deserves further examination.

B. The pu Region Contains ORF4, ORF5, and lef2

Results of further deletions in the pu region are shown in FIG. 3C. All experiments were performed with the co-infection of wild type AcMNPV. Since the only difference between plasmids pAPcmLΔpd and pAPcmLΔpdu is the removal of ORF4, ORF5, and lef2 from the former plasmid, these ORFs were further analyzed. Plasmids pAPcmLΔpu 1, pAPcmLΔpu2, pAPcmLΔpu3, and pAPcmLΔpu4 are constructs that containing ORF4 with a gradual removal of the ORF603 region. The transfection of these plasmids showed that the existence of ORF4 alone has no effect on the activation of the CMVm promoter. Plasmids pAPcmLΔpu5, pAPcmLΔpu6, pAPcmLΔpu7, and pAPcmLΔ603 arc constructs containing a gradual extension of the viral DNA sequence from ORF4 to the lef2 region. The transfection of these constructs showed that plasmid pAPcmLΔ603, the only plasmid that contains all three ORF; (ORF4, ORF5, and lef2), gave rise to full activation of the CMVm promoter. Deletion of ORF4 (pAPcmLΔ4–5, pAPcmLΔ4(1), and pAPcmLΔ4(2)), or both ORF4 and ORF 5 (pAPcmLΔ4–5), from plasmid pAPcmLΔ603, again, completely suppressed the activity of the CMVm promoter. Thus, all three open reading frames, including ORF4, ORF5, and lef2, are required and sufficient for strong activation of this minimal promoter.

C. The pu Region Functions in cis in an Orientation Independent Manner.

Figure 4:
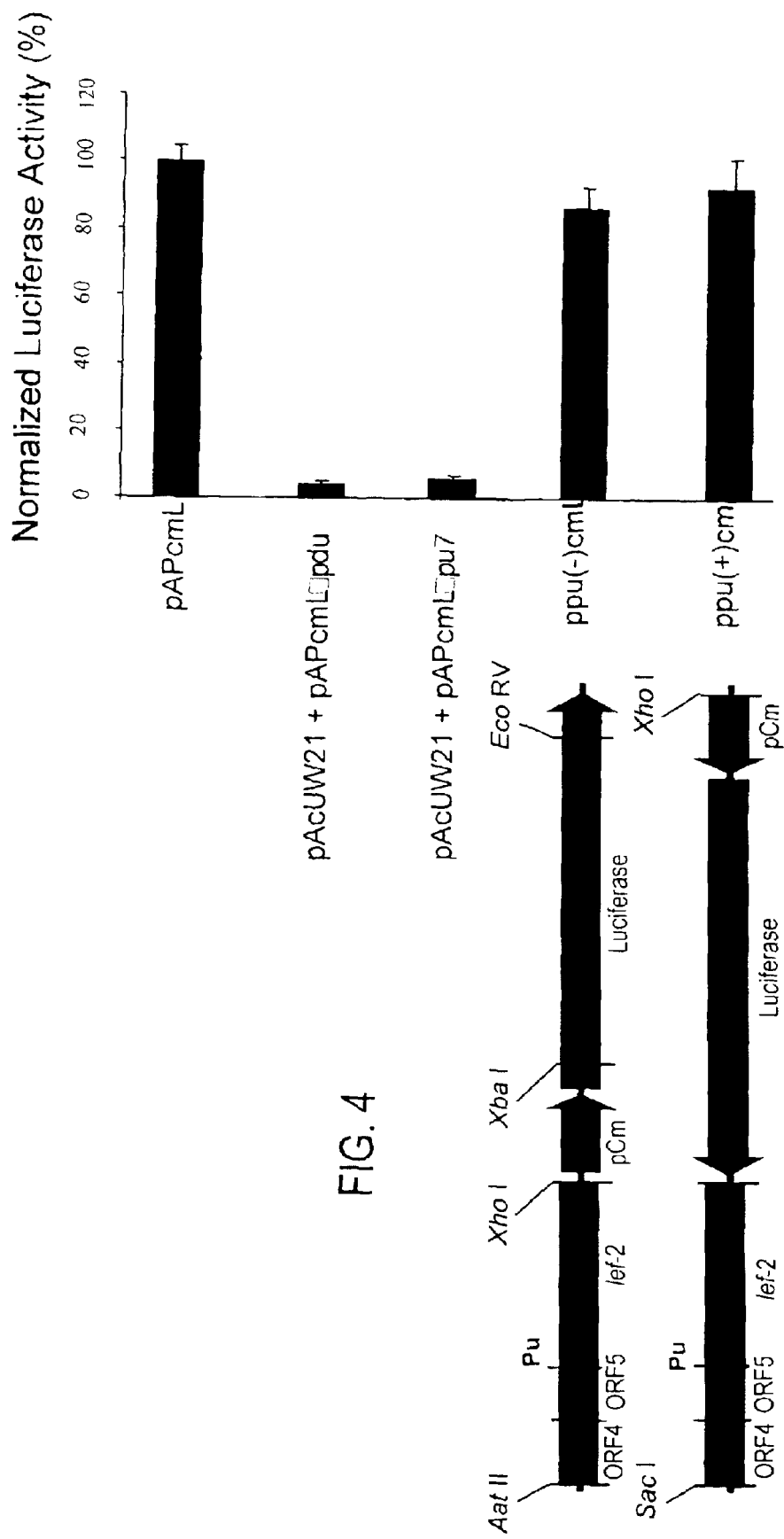
FIG. 4. Positional analysis of pu the sequence for the activation of the CMVm promoter. Plasmid pAPcmL served as a control for 100% luciferase activity. pAcUW21+pAPcmLΔpdu and pAcUW21+pAPcmLΔpu7 were two sets of co-transfection experiments. The pu region, which contains lef-2, ORF4, and ORF 5, is located around 1 to 1500 bp in pAPcmL (FIG. 3C). "−" indicates that the gene or sequence is located upstream of the CMVm promoter, and "+" indicates that its location is downstream of the CMVm promoter. The transfection of different plasmids is shown on the left and normalized luciferase activity is shown on the right.

To determine if the pu sequence activates the CMVm promoter in cis or in trans, plasmid pAcUW21, which contains entire pu sequence, was cotransfected with pAPcmLΔpdu (three ORFs deleted or truncated) or pAPcmLΔpu7 (lef-2 truncated), followed with AcMNPV co-infection (FIG. 4). None of the expression levels in these two deleted clones (pAPcmLΔpdu and pAPcmLΔpu7) were rescued by pAcUW21. When the pu sequence was inserted upstream (pApu(−)cmL) or downstream (pApu(+)cmL) of the CMVm promoter, the luciferase was expressed at the same level as that of pAPcmL (FIG. 4A). These data indicated that the pu sequence must be located in cis in an orientation independent manner for activation of the CMVm promoter.

D. The pu Region and hr Enhancer Function in a Synergistic Manner.

The hrs were shown to be enhancers for the activation of many early baculovirus promoters (Guarino et al., 1986; and Guarino and Summers, 1986). To determine whether these enhancers also function to activate the expression of the CMVm promoter, a complete hr1sequence was inserted upstream to the CMVm promoter. Plasmid pcmL contains a luciferase-coding region, which is driven by the CMVm promoter, and contains no baculovirus sequence. The insertion of the hr1 sequence resulted in new plasmids p+hcmL and pAP+hcmL, both derived from plasmids pcmL and pAPcmL, respectively (FIG. 5A). These newly constructed plasmids were transfected into insect cells with (FIG. 5B) or without (FIG. 5C) the co-infection of baculovirus. FIG. 5C shows that without the co-infection of virus, luciferase was not properly expressed by the transfection of pcmL or pAPcmL, even though the baculovirus lateral fragments were added to the latter plasmid. Similarily, luciferase was not properly expressed in plasmid pAP10 L without the co-infection of the virus.

With the co-infection of baculovirus, the luciferase was better expressed in all plasmids by transfection (FIG. 5B). Although the transfection of plasmids pAPcmL and p+hcmL gave rise to better luciferase activities than the transfection of pcmL, their activities were still weaker than the luciferase activity expressed by the transfection of pAP10L. With the combination of pu and hr1 sequences in plasmid pAP+hcmL, luciferase activity was drastically increased.

Figure 6A:
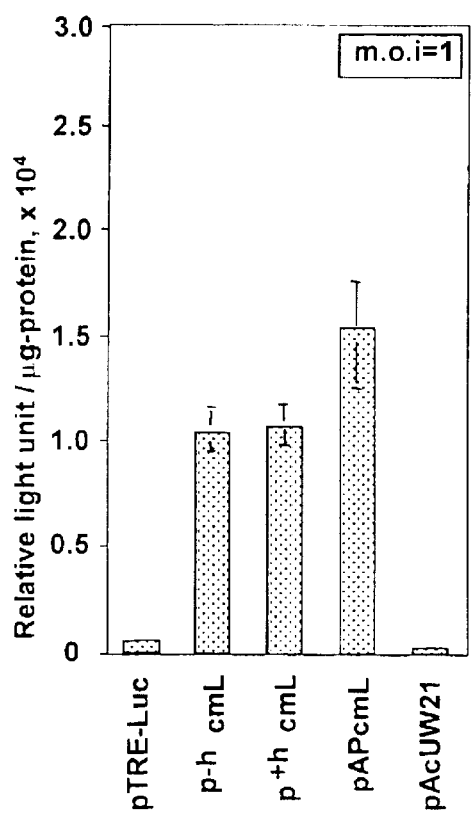
FIG. 6. (Parts A–B) Cooperative activation of the CMVm promoter by hr and/or pu sequences. (A) Activation of the CMVm promoter by the hr enhancer with different orientations (indicated by "+" and "−"). (B) Activation of the CMVm promoter by either multiple hr enhancers or cooperative activation by hr and/or pu sequences; +h, clones contain one hr sequence; +4 h, clones contain 4 hr sequences.
Figure 6B:
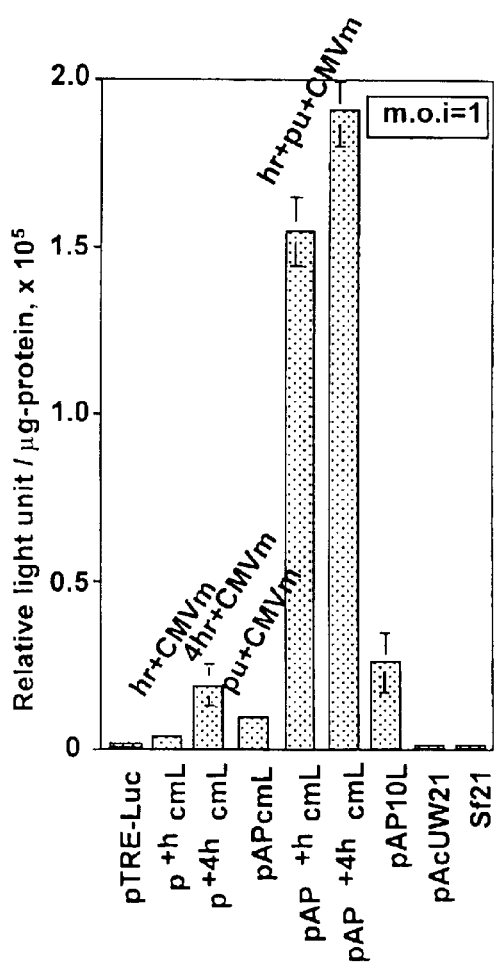

To test and compare whether hr1 enhances the CMVm promoter in an orientation independent manner, the hr1 sequence was inserted in both orientations from upstream of the CMV promoter. FIG. 6A shows that the hr1 sequence can activate the CMVm promoter in an orientation independent manner, just like it enhances the baculovirus promoters. Further experiments showed that more hr1 copies increased the activity of CMVm additively,and very strikingly, that pu and hr1 together function in a synergistic manner (pAP+hcmL). Addition of more hr1 copies to the plasmid. Further increased the CMVm activity additively (pAP+4hcmL, FIG. 6B). Because of synergistic effect of the hr and pu sequences that occurs upon viral coinfection, the expression of the CMVm promoter becomes much stronger than the p10 promoter, one of the very strong very late baculovirus virus promoters, by transient transfection (FIGS. 5, 6B). Thus, a novel set of strong promoters, which are arbitrarily assembled by pu and CMVm (named PCm) or by pu, hr, and CMVm (named PHCm) sequences, can be created in the future for the expression of foreign genes.

Comparison of the Time Course and the Amount of Protein Expression Using PHCm and p10 Promoters.

Figure 7A:
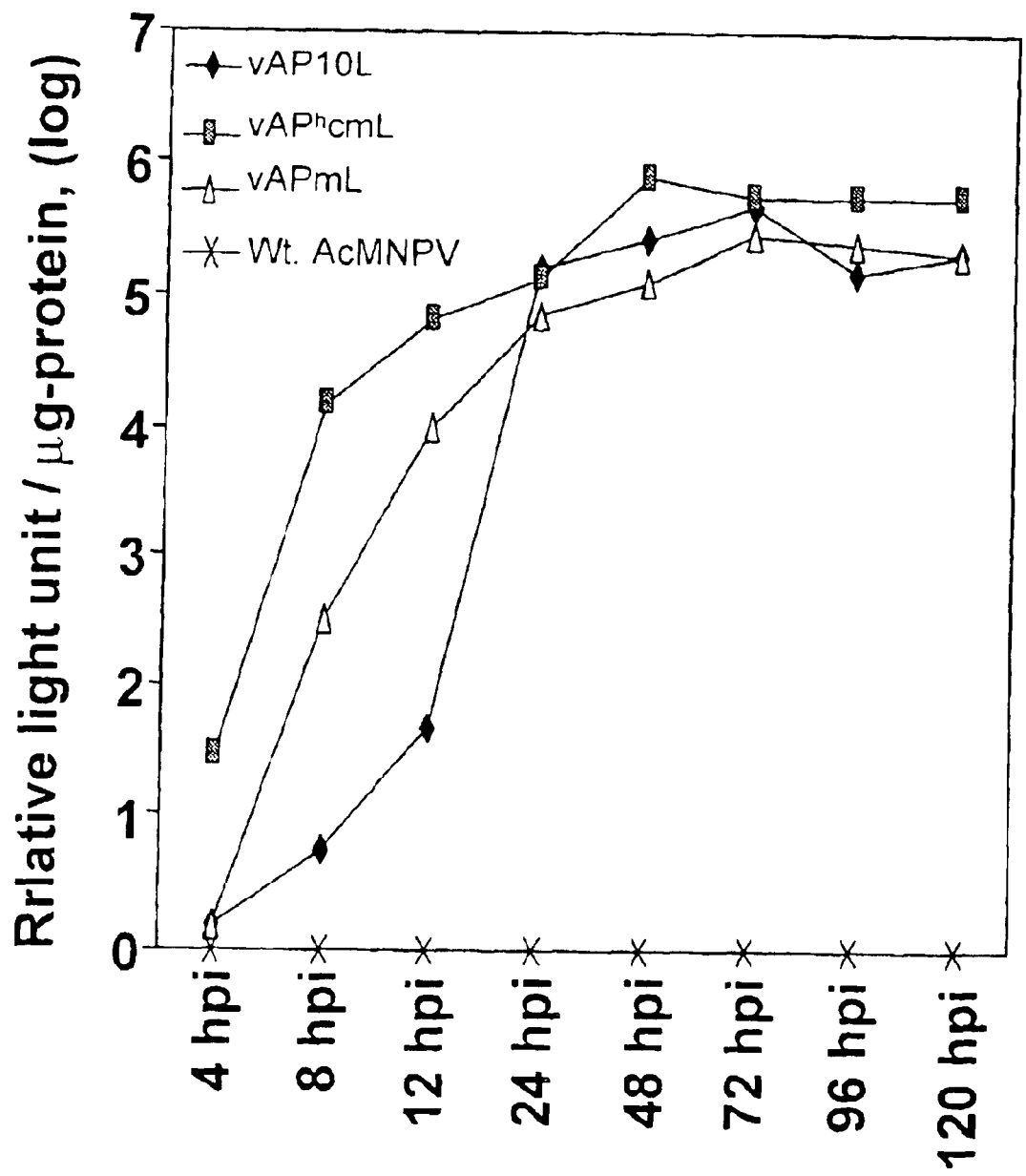
FIG. 7. (Parts A–B) Comparative luciferase expressions by the infection of different recombinant baculoviruses. (A) Western analysis of luciferase expressions by different recombinant viruses. (B) Time course luciferase expressions by different recombinant viruses.

Transfer vector pAPhcmL was further recombined into the genome of baculovirus, resulting in recombinant virus vAPhcmL for the expression of luciferase. The recombinant baculovirus vAP10L, which expresses luciferase by the p10 promoter, was also constructed as a control. The amount of protein produced by these two types of promoters was also compared. Cells infected with different recombinant viruses were harvested at 4 dpi and subjected to Western blot analysis. More luciferase was produced by vAP10 L than by vAPhcmL and vAPcmL. Calibration using standard luciferase (Promega Life Science) showed that the yield of luciferase was 205 µg/ml, 180 µg/ml, and 175 µg/ml, respectively to these three recombinant viruses. Interestingly,p10 promoter although generated more total proteins, extensive luciferase degradation was also found. If measures the intact 60 kD luciferase band, all three recombinant viruses had the same yield (FIG. 7A).

Figure 7B:
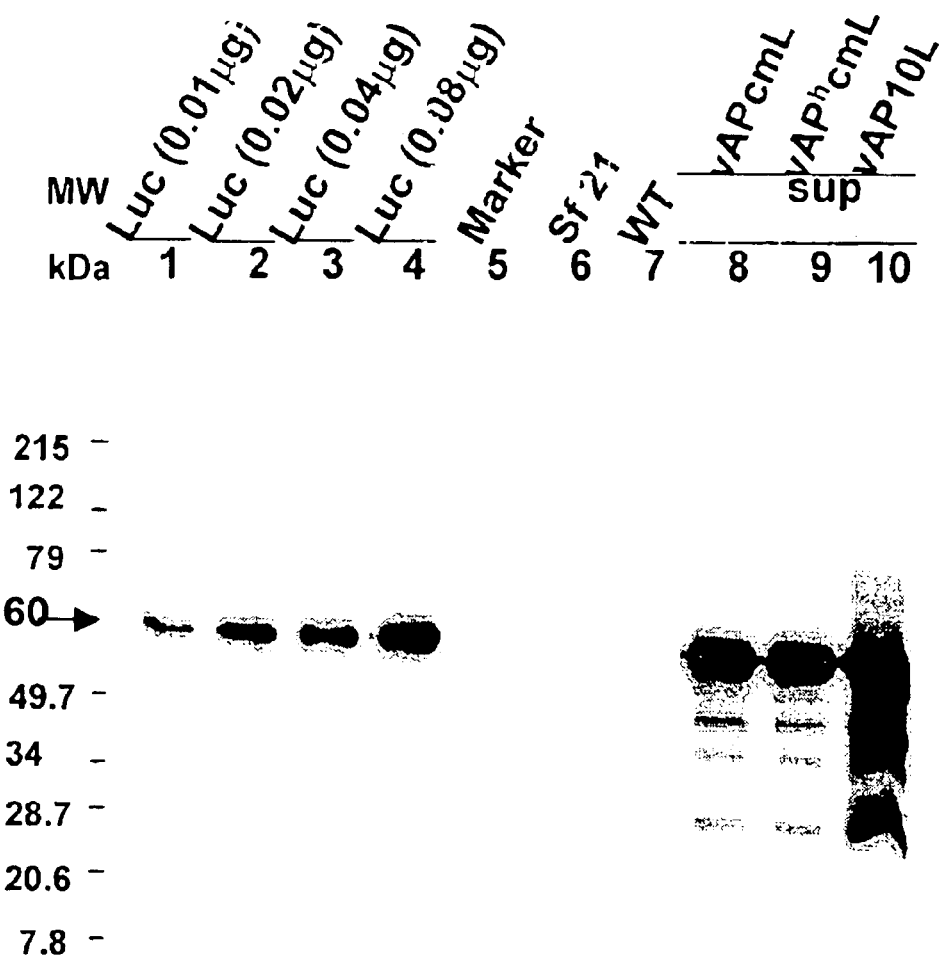

The time course of the luciferase activity expressed by different recombinant viruses was also compared. For the infection of vAPhcmL, luciferase expression was first detected at 4 hours post infection (hpi), quickly increased until 4 days post infection (dpi), and decreased at 5 dpi. However, for the infection of vAP10 L, it took 24 h for the first clear detection of luciferase expression post viral infection. It then increased very quickly until 4 dpi, and also dropped at 5 dpi (FIG. 6B). Although the amount of luciferase expressed by vAP10 L was three times more than that expressed by vAPhcmL (FIG. 7A), the luciferase activity expressed by vAPhcmL was two to three times higher than that expressed by vAP10 L (FIG. 7B).

E. The pu Region is a Universal Enhancer

Figure 8:
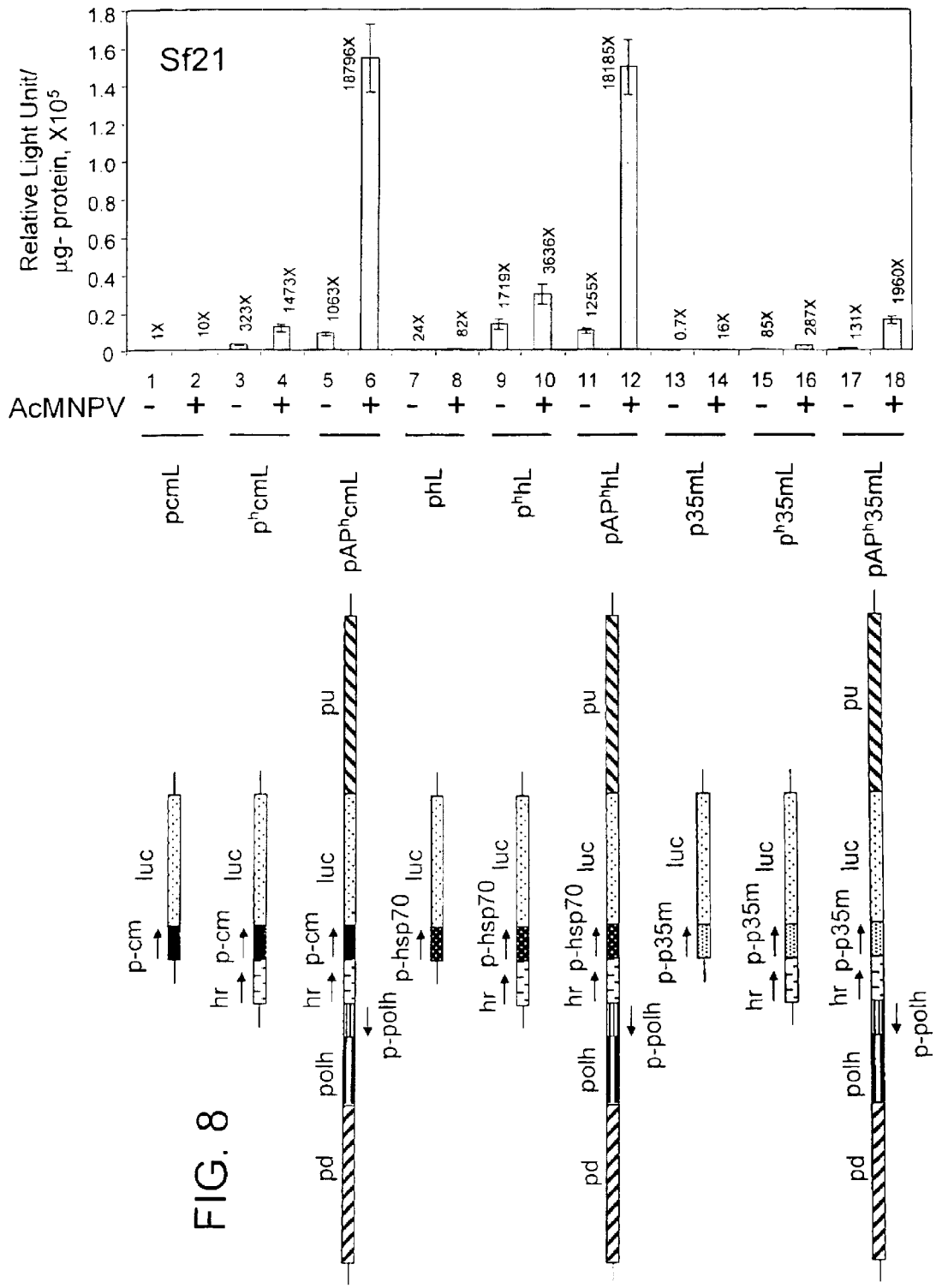
FIG. 8. Activation of different promoters by the pu region. The constructs are on the left and the expressions of luciferase are on the right. Luciferase expression by pcmL without virus co-infection was set as 1× for the calibration of folds of activation of other promoters. The luciferase coding region in plasmids phL, p$^h$hL, and pAP$^h$hL was driven by the full heat shock promoter, hr plus the full heat shock promoter, and pu, hr, plus the full heat shock promoter, respectively. In addition, the luciferase coding region in plasmids p35mL, p$^h$35mL, and pAp$^h$35mL was driven by the baculovirus minimal p35 promoter, hr plus minimal p35 promoter, and pu, hr, plus the p35 minimal promoter, respectively.

To determine whether pu is a universal activator, the full heat shock promoter and minimal p35 promoter were also tested (FIG. 8). We found that pu and hr sequences are able to activate both promoters with or without viral coinfection. Much higher yields were observed upon the coinfection of AcMNPV. Since these experiments involved many constructs under different experimental conditions, the levels of gene expressions vary broadly. In order to deal with this variability, the level of luciferase expression of pcmL without viral coinfection was set as one unit (1×) for the calculation of the expression level of the remaining constructs under different experimental conditions. As shown previously, the PHCm promoter highly expresses luciferase upon the coinfection of AcMNPV (pAPhcmL, FIG. 6). When compared with the 1×basal level of pcmL transfection, more than 18,000×increase could be achieved by pAPhcmL with viral cotransfection (FIG. 8). Similar results were achieved by the transfection of pAPhhL, which is a combination of the pu and hr sequences with the heat shock promoter (named PHH promoter, FIG. 8). The minimal p35 promoter was also highly activated, achieving a level of 1960×activation (pAPh35mL, FIG. 8). However, its luciferase expression was not as strong as when activated by the PHCm and PHH promoters.

All patents and references cited herein are hereby incorporated by reference in their entirety.

What is claimed is:

1. A nucleic acid construct, comprising:
    a nucleotide sequence of less than 10,000 nucleotides, said nucleotide sequence including SEQ ID NO:1, SEQ ID NO:2 and SEQ ID NO:3, wherein a 5' or 3' sequence immediately flanking said nucleotide sequence is different from the 5' or 3' sequence immediately flanking said nucleotide sequence in a AcMNPV genome; and
    a promoter operably linked to a heterologous coding sequence,
    wherein said nucleotide sequence is operably linked to said promoter.
2. The nucleic acid construct of claim 1, wherein said promoter is operably linked to a non-viral coding sequence.
3. The nucleic acid construct of claim 1, wherein said promoter is a viral promoter or a cellular promoter.
4. The nucleic acid construct of claim 1, further comprising a nucleotide sequence encoding a selectable marker.
5. The nucleic acid construct of claim 1, further comprising an hr region operably linked to said promoter.
6. The nucleic acid construct of claim 1, wherein the construct is a plasmid construct.
7. The nucleic acid construct of claim 1, wherein the construct is a viral construct.
8. A host cell containing the nucleic acid construct of claim 1.
9. The nucleic acid of claim 2, wherein the non-viral coding sequence is a mammalian coding sequence.
10. The nucleic acid construct of claim 3, wherein the viral or cellular promoter is a minimal CMV promoter, a p35 promoter, a heat shock promoter, a p10 promoter, or a polyhedrin promoter.
11. The nucleic acid construct of claim 5, wherein said promoter is operably linked to a non-viral coding sequence.
12. The nucleic acid construct of claim 5, wherein said promoter is a viral promoter or a cellular promoter.
13. The nucleic acid construct of claim 5, further comprising a nucleotide sequence encoding a selectable marker.
14. The nucleic acid of claim 11, wherein the non-viral coding sequence is a mammalian coding sequence.
15. The nucleic acid construct of claim 12, wherein the viral or cellular promoter is a minimal CMV promoter, a p35 promoter, a heat shock protein promoter, a p10 promoter, or a polyhedrin promoter.
16. A method of producing a polypeptide, comprising:
    providing a nucleic acid construct including a nucleotide sequence of less than 10,000 nucleotides, said nucleotide sequence including SEQ ID NO:1, SEQ ID NO:2 and SEQ ID NO:3, wherein a 5' or 3' sequence immediately flanking said nucleotide sequence is different from the 5' or 3' sequence immediately flanking said nucleotide sequence in a AcMNPV genome, wherein said nucleotide sequence is operably linked to a promoter that is operably linked to a coding sequence;
    introducing said nucleic acid construct into a cell; and
    allowing said cell to express a polypeptide encoded by said coding sequence, thereby producing a polypeptide.
17. The method of claim 16, wherein the polypeptide is a non-viral polypeptide.
18. The method of claim 16, wherein said promoter is a cellular promoter or a viral promoter.
19. The method of claim 16, wherein the nucleic acid construct is introduced into an insect cell.
20. The method of claim 16, wherein the nucleic acid construct is introduced into the cell by infection with a virus containing the nucleic acid construct.
21. The method of claim 16, wherein the nucleic acid construct is a plasmid construct.
22. The method of claim 16, wherein the nucleic acid construct further includes an hr sequence operably linked to said promoter.
23. The method of claim 17, wherein the polypeptide is a mammalian polypeptide.
24. The method of claim 18 wherein said promoter is a CMV promoter, a minimal CMV promoter, a p35 promoter, a heat shock protein promoter, or a polyhedrin promoter.
25. The method of claim 20, wherein the virus is a baculovirus.
26. The method of claim 21, further comprising the step of co-infecting the cell with a baculovirus.
27. The method of claim 22, wherein the polypeptide is a non-viral polypeptide.
28. The method of claim 22, wherein said promoter is a cellular promoter or a viral promoter.
29. The method of claim 22, wherein the nucleic acid construct is introduced into an insect cell.
30. The method of claim 22, wherein the nucleic acid construct is introduced into the cell by infection with a virus containing the nucleic acid construct.

31. The method of claim 22, wherein the nucleic acid construct is a plasmid construct.

32. The method of claim 27, wherein the polypeptide is a mammalian polypeptide.

33. The method of claim 31, further comprising the step of co-infecting the cell with a baculovirus.

* * * * *